United States Patent [19]

White

[11] 4,155,164
[45] May 22, 1979

[54] APPARATUS FOR APPLYING DENTAL BRACE BRACKETS

[76] Inventor: Velton C. White, 17 N. Broadway, Des Plaines, Ill. 60016

[21] Appl. No.: 760,906

[22] Filed: Jan. 21, 1977

[51] Int. Cl.² .............................................. A61C 7/00
[52] U.S. Cl. ........................................ 32/66; 32/14 A
[58] Field of Search ........................ 32/14 A, 66, 40 R

[56] References Cited

U.S. PATENT DOCUMENTS

| | | | |
|---|---|---|---|
| 1,009,008 | 11/1911 | Asch | 32/40 R |
| 1,518,825 | 12/1924 | Stock | 32/40 R |
| 3,452,436 | 7/1969 | De Woskin | 32/14 A |
| 3,490,145 | 1/1970 | Charrier et al. | 32/14 A |
| 3,871,098 | 3/1975 | Dean | 32/66 |
| 3,924,332 | 12/1975 | Rauch et al. | 32/14 A |
| 3,949,477 | 4/1976 | Cohen et al. | 32/14 A |
| 3,955,282 | 5/1976 | McNall | 32/14 C |
| 3,986,264 | 10/1976 | Faierstein et al. | 32/40 R |

Primary Examiner—Louis G. Mancene
Assistant Examiner—John J. Wilson
Attorney, Agent, or Firm—Trexler, Wolters, Bushnell & Fosse, Ltd.

[57] ABSTRACT

A device for applying a dental brace bracket includes a handle, one or more blades attached to the handle for holding the bracket, a resilient member such as a spring for urging the bracket and bonding agent against the tooth, a heating element attached to the handle and adjacent the holding blades and resilient members for heating the bonding material and means for controlling the temperature and the duration of the heating element.

16 Claims, 9 Drawing Figures

APPARATUS FOR APPLYING DENTAL BRACE BRACKETS

BACKGROUND OF THE INVENTION

This invention relates generally to applying dental brace brackets and more particularly to a new and improved process and apparatus for applying dental brace brackets to the teeth.

A known dental or orthodontic process for realigning the teeth in order to bring them into a more desirable alignment includes the use of structure commonly known as braces. In general, braces comprise a plurality of brackets, one of which is affixed to each of the teeth whose relative re-alignment is desired, and one or more arches or wires attached to the brackets. In use, the stressed arches or wires pull on the brackets in such a way as to urge the teeth into a desired alignment. Each bracket generally comprises a mounting portion having a suitable central groove or throat to engage an aligning arch or wire and or more suitable projections adjacent the throat to receive holding means such as smaller wires to hold the aligning arch or wire in engagement with the throat. The bracket also includes a backing or suitable attaching portion rigidly connected to the mounting for securing the mounting to the tooth, as for example in U.S. Pat. No. 3,052,027 to Wallsheim. Thus, the aligning wire exerts a force on each tooth, through the bracket, to urge the teeth into the desired alignment.

Brackets known in the prior art generally hold the mounting portion to the tooth by means of a band which is fitted around the tooth and which is composed of a suitable material such as a relatively thin metal adapted to be fitted securely to the tooth. The process of applying the band with its attached mounting to the tooth comprises selecting a band of suitable size to be initially fitted around the tooth, urging the band around the tooth and deforming the band by the application of pressure thereto to substantially conform with the contour of the tooth and obtain a firm engagement between band and tooth. It is also known in the prior art to use an adhesive to aid in securing the band or backing to the tooth, as for example in U.S. Pat. No. 3,452,436 to De Woskin and U.S. Pat. No. 3,250,003 to Collito.

It is further often desirable to vary the angle of the mounting throat with respect to the long axis of the tooth to achieve a desired direction of aligning force between the aligning arch or wire and the tooth through the bracket. It is apparent that when using the band commonly offered to attach the bracket to the tooth, the band must be aligned substantially perpendicular to the long axis of the tooth in order to be securely attached to the tooth. Therefore, the choices of orientation of the mounting with respect to the long access of the tooth are limited by the rigid attachment of the mounting to the band. Also, brackets available are generally pre-manufactured with the mounting portion having its throat orientation fixed with respect to the band so that the throat is substantially perpendicular to the long axis of the tooth. Although it is possible to manufacture and provide brackets with the mounting throat attached to the band at various angles, it will be apparent that this approach has numerous shortcomings. Specifically, it would be most convenient for the orthodontist applying the braces to be able to align the throat of each mounting upon the application thereof. In order to do this with presently available band-type brackets, the orthodontist must either attach the mountings to the brackets himself to give each mounting throat the desired alignment, or keep on hand an enormous supply of brackets having mountings with every conceivable angle of alignment and choose among these to meet the needs of each patient. It is apparent that either of these solutions is most inconvenient, expensive and time consuming for the orthodontist. Also, the use of bands is known to have other deleterious side effects such as the promotion of decay of tooth surfaces adjacent or under the bands.

Further, it is apparent that the above-described method of applying brackets to the teeth is not only time consuming but also causes a great deal of discomfort to the patient. Moreover, as the patient must similarly spend a great deal of time in the dentist's chair while the brackets are applied, it is obvious that the process of the prior art is most inconvenient to the patient as well. Additionally, the expense of this process, including the time required to perform it, adds to the cost of the process to the patient. Thus, it would be desirable for both the patient and orthodontist to provide a process and apparatus for applying dental brace brackets that overcomes these shortcomings of the prior art.

OBJECTS AND SUMMARIES OF THE INVENTION

Accordingly, it is an object of the present invention to provide a process and apparatus for applying dental brace brackets which provides a secure attachment of the bracket to the tooth while causing a minimum of discomfort to the patient.

It is another object of the present invention to provide a process and apparatus for applying dental brace brackets, in accordance with the foregoing object, which is more efficient in terms of time and economy than any process or apparatus of the prior art.

Still another object of the present invention is to provide a process and apparatus for applying dental brace brackets, in accordance with the foregoing objects, wherein the mounting throat may be set at any desired angle with respect to the long axis of the tooth concurrently with the attachment of the bracket thereto.

Yet another object is to provide this process and apparatus in a commercially attractive form and at a commercially attractive price.

Briefly, and in accordance with the invention, a process for applying a dental brace bracket comprising a backing and a mounting to a tooth comprises the steps of interposing a heat activatable bonding agent between the backing and the tooth, urging the backing and bonding material against the tooth and heating the bonding material to cause the bonding material to set thereby affixing the bracket to the tooth. In a preferred embodiment the process also includes preparing a surface of the tooth to receive the bracket by applying a suitable preparation to the tooth to adapt a surface of the tooth for adhesion of the bonding material thereto. The process further includes, in a preferred embodiment, the step of controlling the temperature applied to the bonding material during the heating step, and limiting the heating step to a predetermined increment of time.

Similarly, a process for removing a dental brace bracket comprising a backing and a mounting bonded to a tooth by a heat deactivatable bonding material comprises the steps of holding the bracket while heating the bonding material and pulling the bracket away from the tooth as the bonding material is deactivated by the heating. The removal process further includes, in a preferred embodiment, the step of rinsing excess bonding material from the tooth after the bracket has been removed from the tooth. Also, in a preferred embodiment, the process further includes performing normal prophylaxis following the step of rinsing.

Accordingly, an apparatus for applying and removing a dental brace bracket comprising a mounting and a backing comprises a heat activatable and deactivatable bonding material for bonding the backing to a surface of the tooth, and applicator means for releasably holding the bracket and the bonding material against the tooth surface and means for applying heat to the bonding material.

In a preferred embodiment the apparatus further includes means for controlling the temperature and the duration of the heat application. The apparatus further includes, in a preferred embodiment, means for selectively applying the bracket at a predetermined angle with respect to the long axis of the tooth. One applicator apparatus of the prior art is shown in U.S. Pat. No. 3,871,098 to Dean, for example.

The foregoing, as well as other objects and advantages of the present invention will become more readily apparent upon a consideration of the following description together with the accompanying drawings wherein like numerals are used throughout to indicate similar elements and components.

DETAILED DESCRIPTION

Figure 1:
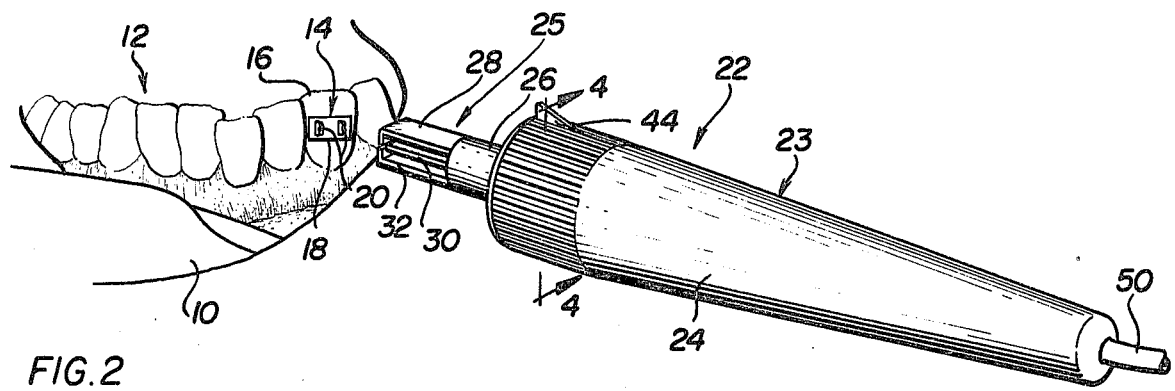
FIG. 1 is a perspective view of a tooth with a dental brace bracket applied thereto in accordance with the process of the present invention, and an apparatus in accordance with the present invention.

Referring now to FIG. 1, a patient's mouth 10 is shown including a number of teeth designated generally by arrow 12. A dental brace bracket 14 applied to a tooth 16 comprises a backing 18 and a mounting 20. A bonding agent (not shown) is interposed between the tooth 16 and the backing 18 of bracket 14. The bonding material may be applied selectively to either the backing 18 or to a suitably prepared surface of the tooth 16.

Alternatively, the bracket 14 may be supplied with a bonding material pre-applied to the backing 18 thereof. A suitable bonding agent comprises a thermoplastic material which at room temperature can be in a solid or plastic state. Upon heating the thermoplastic material becomes fluid but turns to a solid state upon removal of heat therefrom. Preferably, the thermoplastic material may be heated and cooled several times while still retaining these properties. Thus, it is apparent that a strong bond can be formed between the prepared surface of the tooth 16 and the backing 18 of the bracket 14 by applying heat to a thermoplastic bonding agent interposed between the tooth 16 and bracket 14 until the thermoplastic material becomes fluid or moldable, molding the material to the tooth and then removing the heat to allow the material to solidify. The bracket 14 may also be removed from the tooth 16 when desired by applying heat in a similar manner until the thermoplastic bonding agent becomes fluid, and then physically lifting the bracket 14 from the tooth 16. The thermoplastic material used preferably is capable of remaining solid under the normal temperatures to be encountered by the material while it is bonding the bracket 14 to the tooth 16. That is, the thermoplastic material will remain solid at body temperature of substantially 98.7° Fahrenheit and at temperatures somewhat higher than this, as for example during the mastication or consumption of hot food or liquid. However, the thermoplastic material preferably will become fluid so as to facilitate the application of the bracket 18 to the tooth 16 by the application of heat thereto at a temperature and for a period of time well below that which would cause undue discomfort to the patient or any damage to the tooth or surrounding tissue. As a specific example, a thermoplastic material may become fluid at a temperature of between substantially 100° and 125° Fahrenheit and upon application of this temperature thereto for a period of between substantially 15 and 45 seconds.

Alternatively, the bonding agent may comprise a thermoset material. Such a material can be initially, at room temperature, in a relatively fluid or viscous state and thus moldable to the tooth surface. Upon the application of heat thereto, the thermoset material rapidly solidifies. Upon subsequent heating, the thermoset material will not again become fluid. However, a preferred material of the thermoset type would, upon the application of heat at a sufficient temperature and for a sufficient duration, lose its bonding properties and allow the removal of the bracket 18 from the tooth 16. For example, upon heating such a thermoset material at a temperature of between substantially 100° to 125° Fahrenheit for a period of between substantially 15 and 45 seconds, the bond between tooth and bracket is broken. Otherwise, a preferred thermoset type of material exhibits all of the other properties of the thermoplastic material described above.

Either of the above-described types of material may be prepared in advance and held in a suitable container for use as required in bonding brackets to the teeth. For example, the thermoset material in its fluid state may be obtained, ready for use, in a single container of material having a relatively long "shelf life". Alternatively, the thermoset material may be supplied in two separate containers, for example, one containing the bonding agent and a second containing an activating agent to be mixed in a suitable third container at some time prior to the use thereof. Such a "pre-mixed" material preferably has a relatively long, useful life, once the ingredients have been mixed. Similarly, a thermoplastic material as described above may be prepared prior to use as, for example, by placing the material in a suitable heated container to hold it in its fluid state prior to its interposition between bracket and tooth. This material also preferably has a relatively long, useful life while so maintained in a suitable container. Materials having the described properties may be obtained from Richard Bullock, 3500 North Lake Shore Drive, Chicago Ill. 60657. Alternatively, materials having the described properties can be obtained from V. C. Labs., Inc., 17 North Broadway, Des Plaines, Ill. 60016.

Following the step of interposing the bonding material or agent between the bracket 14 and tooth 16, and the heating of the bonding agent, the process according to the present invention may include several preferred steps. When the thermoset material as described above is used, the heating step carried out at the aforementioned temperature and time increments will effect a strong bond between bracket 14 and tooth 16. In the case of a thermoplastic material as described above, the heating step causes the material to become or remain fluid, and the material will set, forming a strong bond between tooth 16 and bracket 18 upon the cooling of the bonding material. In this case, therefore, a preferred step of cooling the tooth 16, bracket 14 and bonding agent may be employed immediately following the heating step. In an alternate embodiment of the process of the present invention, cooling of the tooth may also take place concurrent with the application of heat to the bracket and bonding material in order to protect the tooth and surrounding tissue from excessive heat during the heating step of the process.

In a preferred embodiment, the process for applying the brackets to the teeth further includes the additional step of applying a preparation agent to each tooth or a suitable surface thereof prior to applying the bonding agent and bracket to facilitate adhesion of the bonding material and bracket.

Figure 9:
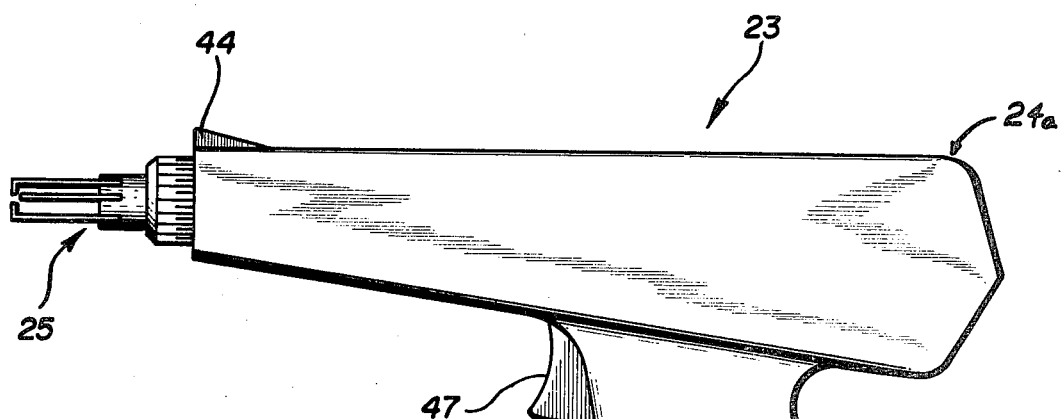
FIG. 9 is a side elevational view of an alternative embodiment of the apparatus of FIGS. 1 and 4.

Having described the process of the present invention, and a suitable bonding agent to be used in the process, an apparatus for carrying out the process is now described in detail. Referring again to the drawings and specifically to FIGS. 1 and 9, an apparatus constructed in accordance with the present invention includes handle means 23 such as a rod or wand 24 of FIG. 1 or a pistol grip 24a of FIG. 9. Means 25 for holding the bracket are rotatably attached to one end of the handle 23 and comprise a generally cylindrical member 26 and three blades 28, 30 and 32 which are adapted to grasp the mounting portion 20 of the bracket 14 as will be described in detail below. The member 26 and blades 28, 30 and 32 are preferably formed from a suitable heat conducting material and further comprise a portion of the heating means of the apparatus.

Figure 2:
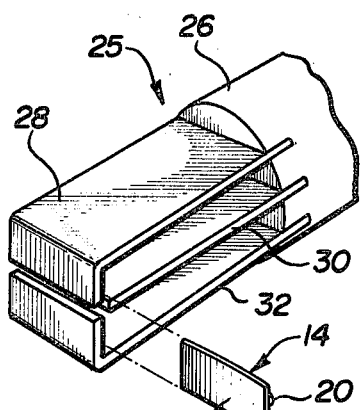
FIG. 2 is an enlarged fragmentary perspective view of a portion of the apparatus of FIG. 1 and a dental brace bracket to be applied thereby.
Figure 3:
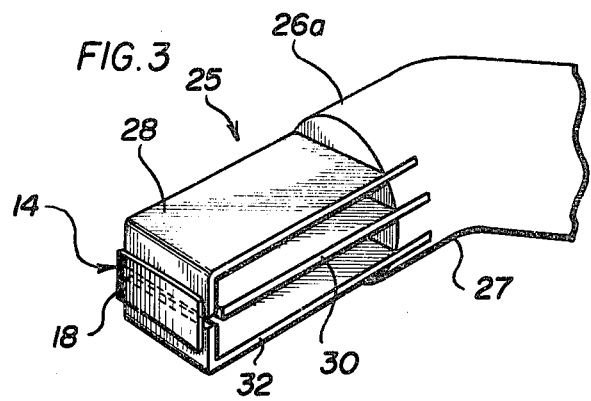
FIG. 3 is a fragmentary perspective view similar to FIG. 2 and illustrating another embodiment of a portion of the apparatus of FIG. 1 together with a dental brace bracket to be applied thereby.
Figure 5:
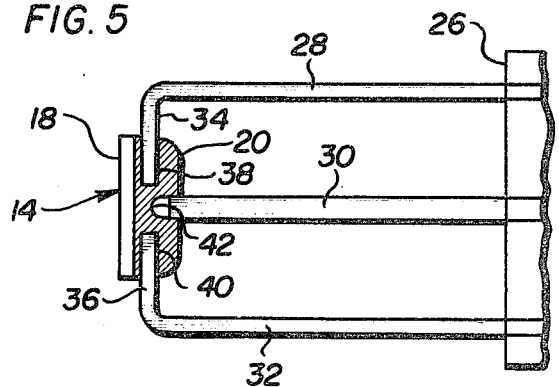
FIG. 5 is an enlarged view of a portion of FIG. 4 together with a dental brace bracket illustrating one embodiment of the present invention.

Turning now to FIGS. 2, 3 and 5 the manner in which the holding means grasp the bracket 14 as illustrated in detail. As described above, bracket 14 comprises backing 18 and mounting 20, as best seen in FIG. 5. Blades 28 and 32 are substantially L-shaped in cross section and include end portions 34 and 36, respectively, bent inwardly at substantially right angles to the generally parallel outwardly extending portions of the blades to form a pair of opposing blade surfaces. The generally opposing blade surfaces of end portions 34 and 36 engage complimentary opposed slots 38 and 40 formed in the mounting 20. Blade member 30 comprises a generally planar surface attached to the member 26 substantially midway between and parallel to the outwardly extending portions of the blades 28 and 32. In the embodiment illustrated in FIGS. 2, 3 and 5, the blade 30 engages a central throat 42 formed in the mounting 20. It will become apparent from the foregoing that the bracket 14 may be fitted upon the holding means comprising the blades 28, 30 and 32 by sliding the bracket 18 as indicated by the dotted lines of FIG. 2 so as to cause the mounting 20 to engage the blades 28, 30 and 32 as shown in FIG. 5, resulting in the bracket 14 being held in a suitable position to be applied to the tooth as seen best in FIGS. 3 and 5.

FIG. 3 also illustrates an alternate embodiment of the holding means 25. A generally cylindrical member 26a is provided with a bend or curve 27 formed therein. While, in the embodiment of FIG. 1, the holding means 25 comprising the member 26 and blades 28, 30 and 32 is generally coaxial with the handle 24, in this alternate embodiment the bend 27 of the member 26a results in the holding means 25 comprising member 26a and the blades 28, 30 and 32, being offset at a predetermined angle to the axis of the handle 24. It should be apparent that the first embodiment is thus especially adapted for the application of a bracket generally to the front teeth of a patient, whereas the second embodiment is especially adapted for the application of a bracket to the side or back teeth of a patient.

Figure 4:
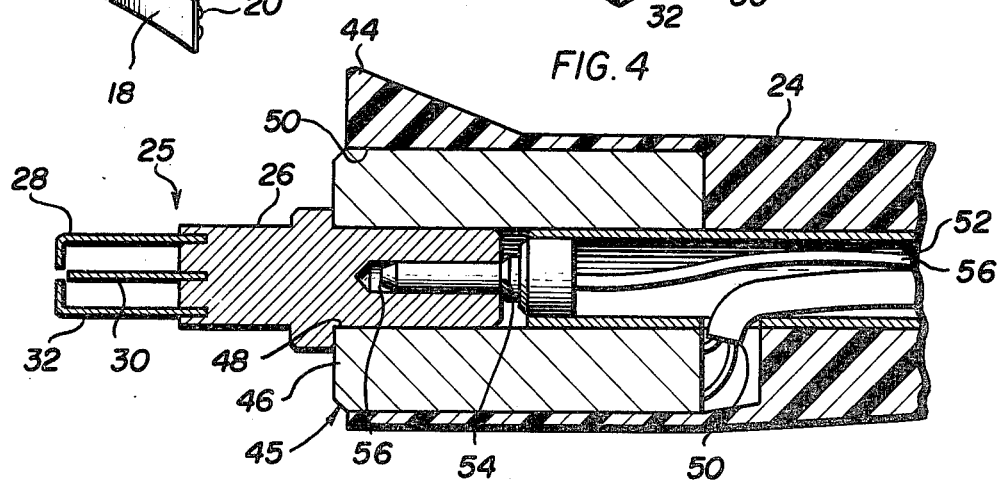
FIG. 4 is a side elevational view taken generally along line 4—4 of FIG. 1.
Figure 8:
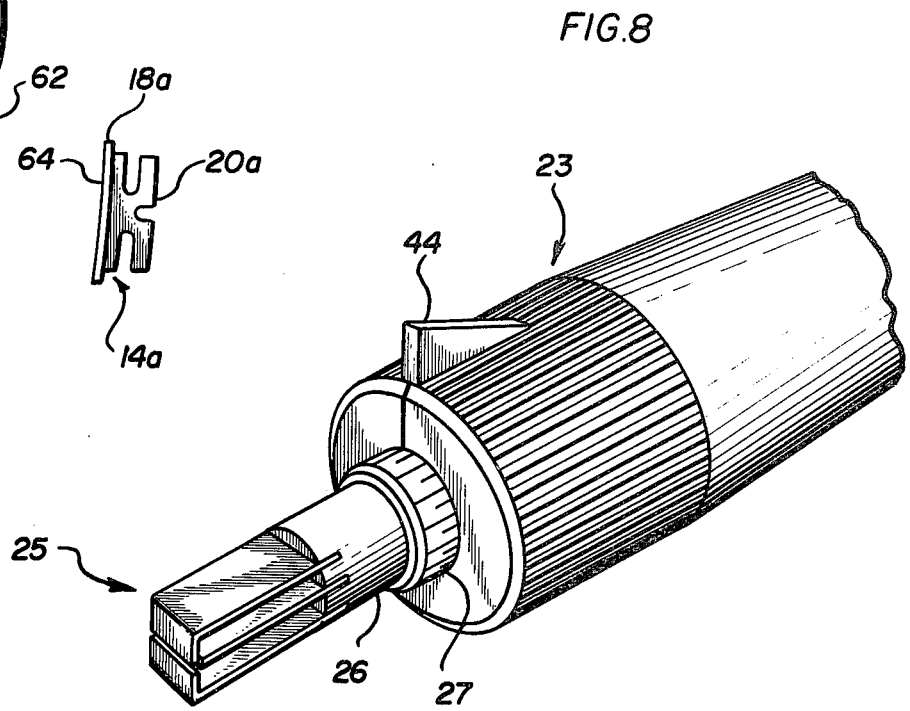
FIG. 8 is a perspective view of a portion of the apparatus of FIG. 4 illustrating additional features thereof.

Attention is now directed to FIGS. 1, 4 and 9 wherein additional features of the apparatus are illustrated in further detail. A sight 44 comprising a relatively thin raised strip of material is formed at the end of the handle 24. The member 26 of the holding means 25 is rotatably mounted in an opening 48 provided therefore at the end portion of handle 24 below the sight 44 which is substantially in alignment with a diameter of the generally cylindrical member 26. In a preferred embodiment as best seen in FIG. 8, a number of indicator markings 27 are formed around the circumference of member 26 to aid in setting and giving visual indication of the angle of the holding means 25 with respect to the vertical axis of the sight 44. Thus, the bracket 14 may be mounted on the tooth 16 with the mounting 20 and specifically the central throat 42 thereof aligned at a desired angle with respect to the vertical axis of the tooth 16. For example, by first rotating the member 26 to align an indicator marking corresponding to the desired angle with the sight 44 and then, upon applying the bracket 14 to the tooth 16 aligning the sight 44 along the vertical axis of the tooth, the bracket 14 may be applied at the desired angle with respect to the long axis of the tooth 16.

Figure 6:
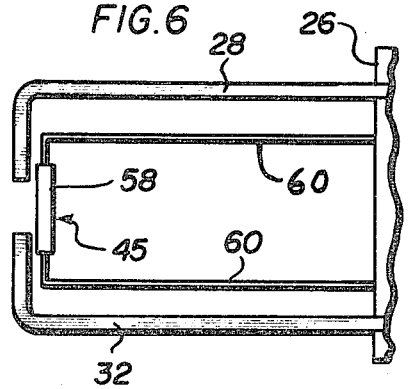
FIG. 6 is an enlarged view, similar to FIG. 5, illustrating another embodiment of the apparatus of the present invention.

The apparatus of the present invention also includes heating means 45 as best seen in FIGS. 4 and 6. In FIG. 4, one embodiment of suitable heating means 45 is illustrated as a metal spool member 46 engaged in a suitable opening 50 provided therefore in the handle 24. The spool 48 is provided with suitable connections such as wire 50 to an external source of electric power (not shown). The wire 50 extends through a suitable central opening 52 provided therefore in the handle means 23 and exits at the rear end of the handle means 23 as best seen in FIGS. 1 and 9. Thus, as illustrated in FIG. 4, the member 26 of the holding means is rotatable inside a suitable opening 48 provided therefore in the spool 46 which in turn is non-rotatably inserted in an opening 50 provided therefore in the handle 24. A suitable on-off switch for the heating means 45 is also provided, and may be mounted upon the handle 25, as switch 47 of FIG. 9, or be in the form of a foot switch (not shown).

A temperature control means is also provided including a temperature sensor 54 which may be, for example, a thermocouple disposed inside an opening 56 provided therefore in the member 26 of the holding means to sense the temperature of the holding means. The temperature sensing means 54 is connected by a suitable means such as a line 56 which is also disposed inside the aforementioned opening 52 in the handle 24 to exit along with cable 50 to a suitable external temperature control device (not shown) for regulating the power supplied through the wire 50 to the heating device. Thus, the bonding material is heated to a predetermined, regulated temperature when it comes in contact with the backing 18 of the bracket 14 which in turn is heated by the conduction of heat through the blades 28, 30 and 32 and the member 26 which, as described above, are formed of a suitable heat conducting material, to conduct the heat from the spool or heating element 46 to the bracket 14.

An alternate embodiment of a suitable heating means comprises a heating resistor 58, as seen in FIG. 6. In the embodiment of FIG. 6, the heating resistor 58 is connected by suitable means such as lead wires 60 back into the handle 24 and therethrough, in a manner similar to the wire 50, to a suitable source of electric power. In this embodiment, the heating resistor 58 is positioned relative to the blades 28, 30, and 32 so as to come directly in contact with the bracket 14 via the mounting 20. It is apparent that in this embodiment, the blade 30 of FIG. 5 will be eliminated and the bracket will be held by blades 28 and 32 only. Also, the blades 28 and 32 and member 26 comprising the holding means 25 need not be of heat conducting material in this embodiment.

Although two specific embodiments of heating means have been shown and described herein, it is not intended to so limit the present invention to the heating means described. Other heating means such as, for example, a ribbon heater or induction heating may also be readily adapted to cooperate with the apparatus described to form a part of the present invention.

Figure 7:
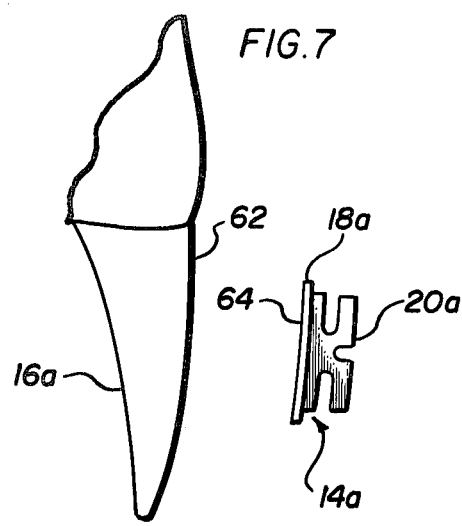
FIG. 7 is a side elevational view of a dental brace bracket and a tooth illustrating further features of the process of the invention.

Turning now to FIG. 7, a second type of bracket 14a is shown in conjunction with a tooth 16a to which it may be applied in accordance with the present invention. It will be noted that the front or outer surface 62 of the tooth 16a exhibits a slight curvature. Similarly, the backing 18a of the bracket 14a is provided with a curvature 64 which is somewhat greater than the curvature of the surface 62 of the tooth 16a. In accordance with the present invention, a preferred process for applying the bracket 14a to the tooth 16a would further include urging the curvature 64 of bracket 14a against the curvature of the surface 62 of the tooth 16a so as to create a suction force therebetween. This results in a decrease in the curvature of the backing surface 64 to conform to the curvature of the tooth surface 62. It is apparent that this suction type of mount increases the strength of the forces bonding the bracket 14a to the tooth 16a and aids the interposed bonding agent in securing the bracket to the tooth. In the embodiment illustrated in FIG. 7, the apparatus also further includes urging or biasing means to press the bracket 14a against the tooth 16a with sufficient force to cause curvature 64 to conform to curvature 62. This biasing means may be in the form of a spring (not shown) urging member 26 and the attached blades 28, 30 and 32 against the tooth surface as the handle 24 is pressed in a direction towards the tooth 16.

The apparatus of the present invention may include, in a preferred embodiment, cooling means. The cooling means (not shown) may comprise, for example, a tube or jet mounted upon the handle 24 and positioned so as to direct a stream of cooling material such as air or mater upon the tooth 16 and surrounding tissue to protect the same against any possible harm from the heating means. Such a cooling means would further promote the setting of a bonding material, such as a thermoplastic material, upon the termination of the action of the heating means thereupon.

While specific embodiments of the invention have been shown and described herein, changes and modifications which may occur to those skilled in the art will be understood as forming a part of the present invention insofar as they fall within the spirit and scope of the appended claims.

The invention is claimed as follows:

1. An apparatus for applying and removing a dental brace bracket comprising a mounting and a backing to a tooth, said backing being coated with a heat activatable bonding material, said apparatus comprising: handle means for holding the apparatus, holding means attached to said handle means for holding the bracket against the tooth, means connected to said handle means for selectively heating the bonding material, means connected to the handle means for controlling the temperature and duration of said heating means, and wherein said holding means is rotatable with respect to the handle means for selectively applying said bracket at a predetermined angle with respect to the long axis of the tooth.

2. An apparatus according to claim 1 wherein said mounting includes a central throat and opposed side slots and said holding means comprises first and second blade means for interfitting with said opposed side slots.

3. An apparatus according to claim 2 wherein said holding means further includes third blade means for interfitting with said central throat.

4. An apparatus according to claim 3 further including means for selectively setting a predetermined angle of rotation of said holding means relative to said handle means, corresponding to said predetermined angle of the bracket with respect to the long axis of the tooth.

5. An apparatus according to claim 4 further including sight means attached to said handle means and indicator means formed on said rotating means to align with said sight means to select and indicate said predetermined angle.

6. An apparatus according to claim 5 wherein said controlling means includes a source of power connected to said heating means and switch means connected to said source of power for selectively turning said source of power on and off.

7. An apparatus according to claim 6 wherein said controlling means further includes temperature sensing means adjacent to said heating means and regulating means for said source of power connected to said temperature sensing means to regulate the temperature of the heating means.

8. An apparatus according to claim 6 wherein said handle means comprises a pistol grip and said switch means is mounted upon said pistol grip.

9. An apparatus according to claim 6 wherein said handle means comprises a wand and said switch means is mounted upon said wand.

10. An apparatus according to claim 6 wherein said handle means comprises a wand and said switch means comprises a foot switch disposed in a location remote from said handle means.

11. An apparatus according to claim 6 wherein said heating means comprises a metal spool attached to said handle means and to said holding means.

12. An apparatus according to claim 6 wherein said heating means comprises a ribbon heater attached to said handle means and to said holding means.

13. An apparatus according to claim 6 wherein said heating means comprises an induction heater attached to said handle means and to said holding means.

14. An apparatus according to claim 6 wherein said heating means comprises a heating resistor attached to said holding means and to said handle means.

15. An apparatus according to claim 6 wherein said holding means is substantially co-axial with said handle means.

16. An apparatus according to claim 6 wherein said holding means is disposed at an angle to said handle means.

* * * * *